(12) United States Patent
Araya et al.

(10) Patent No.: US 10,821,203 B2
(45) Date of Patent: *Nov. 3, 2020

(54) COMPOSITION AND DRESSING WITH NITRIC OXIDE

(71) Applicant: PQ Silicas UK Limited, Cheshire (GB)

(72) Inventors: Abraham Araya, Wirral (GB); Alan Reginald Minihan, Wallasey (GB); Paul Matthew Robbins, Worsley (GB); Sonya Theresa Broderick, Widnes (GB); Michael J. Waring, Wirral (GB)

(73) Assignee: PQ Silicas UK Limited, Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/705,775

(22) Filed: Sep. 15, 2017

(65) Prior Publication Data

US 2018/0000985 A1 Jan. 4, 2018

Related U.S. Application Data

(63) Continuation of application No. 14/458,630, filed on Aug. 13, 2014, which is a continuation of application No. 13/130,233, filed as application No. PCT/GB2009/002718 on Nov. 20, 2009, now abandoned.

(30) Foreign Application Priority Data

Nov. 21, 2008 (GB) .................................. 0821345.6

(51) Int. Cl.
| | |
|---|---|
| *A61L 26/00* | (2006.01) |
| *A61L 15/18* | (2006.01) |
| *A61L 15/44* | (2006.01) |
| *A61L 15/58* | (2006.01) |

(52) U.S. Cl.
CPC ........... *A61L 26/0052* (2013.01); *A61L 15/18* (2013.01); *A61L 15/44* (2013.01); *A61L 15/58* (2013.01); *A61L 26/0004* (2013.01); *A61L 26/0066* (2013.01); *A61L 2300/114* (2013.01); *A61L 2300/602* (2013.01); *A61L 2300/802* (2013.01)

(58) Field of Classification Search
CPC .. A61L 26/0004; A61L 26/0066; A61L 15/18; A61L 26/0052; A61L 15/58; A61L 15/44; A61L 2300/114; A61L 2300/602; A61L 2300/802
See application file for complete search history.

(56) References Cited

U.S. PATENT DOCUMENTS

| | | | |
|---|---|---|---|
| 3,339,546 A | 9/1967 | Chen | |
| 4,525,410 A | 6/1985 | Hagiwara et al. | |
| 4,551,490 A | 11/1985 | Doyle et al. | |
| 4,775,585 A | 10/1988 | Hagiwara et al. | |
| 4,822,349 A | 4/1989 | Hursey et al. | |
| 5,100,671 A | 3/1992 | Maeda et al. | |
| 5,633,010 A | 5/1997 | Chen | |
| 5,814,666 A | 9/1998 | Green et al. | |
| 6,143,798 A | 11/2000 | Jensen et al. | |
| 6,146,654 A * | 11/2000 | Kubo ................... | A61K 9/7023 424/443 |
| 6,191,216 B1 | 2/2001 | Ganster et al. | |
| 6,261,594 B1 | 7/2001 | Smith et al. | |
| 6,357,678 B1 | 3/2002 | Hu et al. | |
| 6,573,419 B2 | 6/2003 | Naimer | |
| 6,592,888 B1 * | 7/2003 | Jensen ..................... | A61L 15/18 424/443 |
| 7,563,933 B2 | 7/2009 | Meier et al. | |
| 2001/0009831 A1 | 7/2001 | Schink et al. | |
| 2002/0054919 A1 | 5/2002 | Hochwalt et al. | |
| 2003/0170453 A1* | 9/2003 | Foss ........................ | A01N 57/16 428/373 |
| 2004/0234474 A1 | 11/2004 | Berlat | |
| 2006/0269620 A1* | 11/2006 | Morris ..................... | A61K 8/19 424/684 |
| 2007/0112218 A1* | 5/2007 | Meier ..................... | B01D 15/00 564/479 |
| 2008/0069848 A1 | 3/2008 | Peters | |
| 2008/0069863 A1 | 3/2008 | Peters | |
| 2009/0098187 A1 | 4/2009 | Peters et al. | |
| 2009/0148482 A1 | 6/2009 | Peters | |
| 2009/0226504 A1 | 9/2009 | Peters | |

(Continued)

FOREIGN PATENT DOCUMENTS

| | | |
|---|---|---|
| CN | 101189032 A | 5/2008 |
| EP | 0888783 A1 | 1/1999 |

(Continued)

OTHER PUBLICATIONS

International Search Report for PCT/GB2009/002718 dated Oct. 22, 2010 (Form PCT/ISA/210).

(Continued)

*Primary Examiner* — Doan T Phan
(74) *Attorney, Agent, or Firm* — Buchanan Ingersoll & Rooney PC

(57) ABSTRACT

A dressing composition for use as a skin dressing comprises an elastomeric-adhesive composition, and a zeolite comprising releasably adsorbed nitric oxide. The zeolite may comprise a transition metal cation such as Co, Fe, Mn, Ni, Cu, Zn, Ag or a mixture thereof as an extra-framework metal cation, preferably Zn. The elastomeric adhesive composition may be a hydro-colloid-adhesive composition comprising, hydrocolloid and elastomer. The dressing composition releases nitric oxide, which may have beneficial effects, when used on wounds or moist skin, with a substantially constant release rate over a long period of time. A dressing including a layer of the dressing composition has a backing layer and may have a release liner removably attached to the skin-contacting surface of the dressing layer.

19 Claims, 4 Drawing Sheets

(56) References Cited

U.S. PATENT DOCUMENTS

| | | |
|---|---|---|
| 2010/0016790 A1 | 1/2010 | Peters |
| 2010/0280427 A1 | 11/2010 | Larsen |

FOREIGN PATENT DOCUMENTS

| | | |
|---|---|---|
| EP | 1159972 A2 | 12/2001 |
| EP | 1731176 A1 | 12/2006 |
| JP | 5285209 | 11/1993 |
| JP | 2007526867 A | 9/2007 |
| WO | 0121148 A1 | 3/2001 |
| WO | 0222060 A1 | 3/2002 |
| WO | 2005003032 A1 | 1/2005 |
| WO | 2005063681 A1 | 7/2005 |
| WO | 2006064056 A2 | 6/2006 |
| WO | 2006084913 A2 | 8/2006 |
| WO | 2006084914 A2 | 8/2006 |
| WO | 2006100155 A1 | 9/2006 |
| WO | 2006128743 A1 | 12/2006 |
| WO | 2007028657 A1 | 3/2007 |
| WO | 2007092350 A1 | 8/2007 |
| WO | 2008062160 A1 | 5/2008 |
| WO | 2009010068 A1 | 1/2009 |

OTHER PUBLICATIONS

Written Opinion of the International Searching Authority dated Oct. 22, 2010 (Form PCT/ISA/237).

Wheatley et al., "No-Releasing Zeolites and Their Antithrombotic Properties" Journal of the American Chemical Society, Dec. 20, 2005 American Chemical Society, Washington. D.C., vol. 128, No. 2, pp. 502-509.

Mowbray et al., "Topically Applied Nitric Oxide Induces T-Lymphocyte Infiltration in Human Skin, but Minimal Inflammation", Journal of Investigative Dermatology (2008), vol. 128, pp. 352-360.

Pavelic et al., "Immunostimulatory Effect of Natural Clinoptilolite as a Possible Mechanism of its Antimetastatic Ability", J. Cancer Res Clin Oncol (2002), vol. 128, pp. 37-44.

Zhang et al., "Removal of Nitrogen Monoxide on Copper Ion-Exchanged Zeolites by Pressure Swing Adsorption", Langmuir (1993), vol. 9, pp. 2337-2343.

Palevic, et al. (2003) "Medical Application of Zeolites". Handbook of Zeolite Science and Technology, Chapter 24, pp. 1-32.

Silberberg, Martin, (2006) "Chapter 14: Periodic patterns in the main-group element". Chemistry: The Molecular nature of Matter and Change, Fourth Edition, pp. 1-26, http://facweb.northseattle.edu/sremington/Chapter14_odd_probs.pdf, accessed on Oct. 16, 2012.

Masters, et al. Effects of nitric oxide releasing poly(vinyl alcohol) hydrogel dressings on dermal wound healing in diabetic mice, Wound Rep. Reg. 2002, vol. 10, pp. 286-294.

Japanese Office Action dated Jan. 21, 2014 for Japanese Patent Application No. 2011-536944.

Xiao et al. (2007). "The Adsorption, storage and release of nitric oxide using ion exchanged zeolites". Studies in Surface Science and Catalysis, 170: 902-909.

"Alginate based bilayer hydrocolloid films as potential slow-release modern would dressing" by Hnin-Ei Thu, Mohd Hanif Zulfakar, Shiow-Fern Ng. International Journal of Pharmaceutics 434 (2012) 375-383, 2012.

"Alginate Hydrogels Coated with Chitosan for Wound Dressing" by Maria Cristina Staccia, Giovanna Gomez d'Ayala, Ida Romano, Adriana Oliva, and Paola Laurienzo,; Mar. Drugs 2015, 13, 2890-2908; Open Access: Marine Drugs; www.mdpi.com/journal/marinedrugs; Published: May 11, 2015.

\* cited by examiner

COMPOSITION AND DRESSING WITH NITRIC OXIDE

CROSS REFERENCE TO RELATED APPLICATIONS

This application is a continuation application claiming priority to U.S. patent application Ser. No. 14/458,630, filed Aug. 13, 2014, which in turn claims priority to U.S. patent application Ser. No. 13/130,233, filed Aug. 3, 2011 which is the United States national phase under 35 U.S.C. § 371 of PCT International Patent Application No. PCT/GB2009/002718, filed on Nov. 20, 2009 and claiming priority to United Kingdom Application No. 0821345.6, filed on Nov. 21, 2008, and incorporated by reference herein.

INTRODUCTION

The present invention relates to compositions for use in dressings for application onto skin, for instance as dressings for the treatment of wounds, pre-treatment of skin, ostomy seals, neuropathy treatment, treatment of fungal disorders, transdermal drug release and the like. In particular, it relates to compositions comprising elastomeric adhesive and zeolite wherein the zeolite comprises releasably adsorbed nitric oxide.

BACKGROUND

The 1998 Nobel Prize for Physiology or Medicine was awarded in 1998 for the discovery that endogenous nitric oxide is responsible for endothelium-dependent smooth muscle relaxation. Nitric oxide (NO) is also a vasodilator, and increases blood flow through blood vessels. Nitric oxide is also an important factor in controlling and preventing platelet adhesion in the blood and may consequently act against thrombus formation. It also plays an important role in the immune system, inflammatory reaction mechanisms and in neurotransmission.

The delivery of nitric oxide to the skin may also have therapeutic benefits for treatment of peripheral circulatory problems or neuropathy (such as may arise from arthritis or Raynaud's condition. Nitric oxide also exhibits anti-pathogenic behaviour and may be used for treatment of bacterial, viral and fungal infections, and at suitable concentrations it can be cytotoxic, for instance it is effective as a cytotoxic agent on human haematological malignant cells such as from patients with leukaemia or lymphoma.

Nitric oxide may also play a part in wound healing and angiogenesis. In particular, it has been found that delivery of exogenous nitric oxide to wounds and ulcers may assist healing, particularly for patients where healing is otherwise slow (such as in elderly or diabetic patients). Nitric oxide may also lead to a reduction in inflammatory processes at wound sites. Nitric oxide may also be effective for reduction in inflammation and scarring arising from medical articles (such as stents, catheters, pacemakers, etc.) implanted within a human or animal body.

The delivery of NO as a gas is fraught with problems, and its short half-life, once released into the body, is a further problem in its use as for treatment. NO is toxic in high concentrations and may have negative effects if applied in excessive amounts to the body.

Various methods of nitric oxide delivery are known in the art. These include: compounds which i) release NO spontaneously in the bloodstream, ii) compounds which are metabolised to generate NO, iii) compounds releasing NO upon photoactivation, iv) polymers which hold and release NO, v) production of NO from a chemical reaction.

The various known NO releasing agents have problems such as lack of targeting ability or selectivity, potentially carcinogenic or toxic by-products, need for specific activation, difficulties in manufacture or difficulties with controlled release.

In the international patent application published as WO 2005/003032, zeolites comprising releasably adsorbed nitric oxide were disclosed and proposed as suitable agents for targeted release of nitric oxide. The NO-carrying zeolites exemplified in this aforementioned publication were prepared by ion-exchange of ammonium zeolites.

Because nitric oxide is active in many biological processes, targeted delivery of exogenous NO is desirable. Hence, the delivery of exogenous nitric oxide from a dressing is a potentially attractive therapy for a number of ailments and for other uses requiring delivery of NO to skin or body orifices.

Hence, there is a need to provide dressings and dressing compositions which are capable of providing steady topical release of endogenous nitric oxide and which overcome some or all of the problems of the prior art.

SUMMARY

One object of the present invention, amongst others, is to provide a composition, for use in skin dressings, which provides delivery of nitric oxide to the skin over an extended period of time. An object of the invention is to provide a dressing composition having an anti-pathogenic effect. Another object of the invention is to provide a safe and convenient topical, targeted delivery system for nitric oxide, which overcomes some of the problems in the prior art.

A first aspect of the invention provides a dressing composition for use as a skin dressing comprising:
i) an elastomeric adhesive composition, and
ii) a zeolite comprising releasably adsorbed nitric oxide.

A second aspect of the invention provides a dressing for application to skin comprising a backing layer holding a dressing layer comprising a skin contacting surface and a dressing composition according to the first aspect of the invention. The dressing may further comprise a release liner removably attached to the skin-contacting surface of the dressing layer. The dressing of the second aspect of the invention may be a self-adhesive dressing or may need to be held to the skin by some other means such as a bandage or dressing cover.

DETAILED DESCRIPTION

Figure 1:
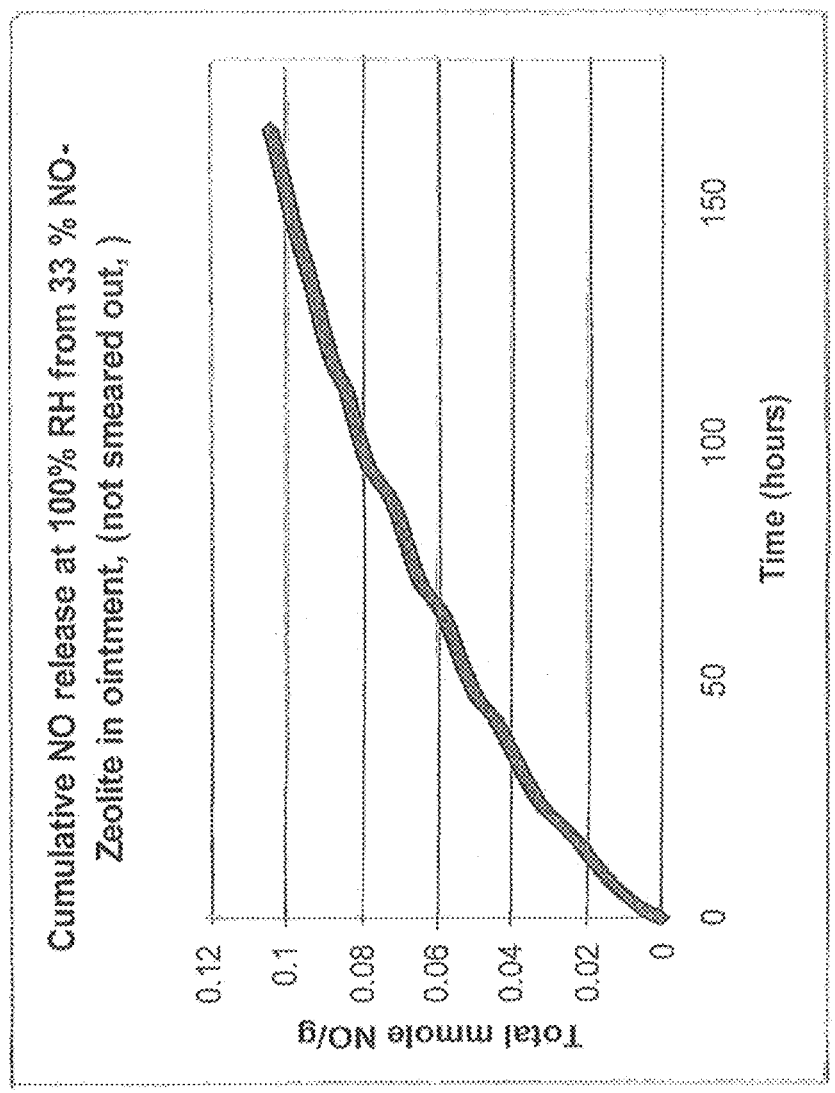
FIG. 1 is a graph showing the cumulative NO release (in mmol NO per gram of Zeolite-NO present in the sample) over time (in hours) at 100% relative humidity from a non-smeared sample of Ointment A according to Example 2.

Suitable and preferred features of the invention will now be set out. These various features may be used in suitable combinations with each other unless otherwise specified.

A zeolite is a crystalline aluminosilicate, typically represented by the empirical formula I;

$$\Sigma_j[z_i(M^i{}_{2/ni}O)].Al_2O_3.xSiO_2.yH_2O \qquad \text{I}$$

wherein $M^i$ represents a cationic moiety (usually a metal, known as an extra-framework cation) having a valency of $n_i$, where $n_j$ may range from 1 to 6, typically 1 to 4, but more usually 1 to 3, generally 1 or 2. $M^1$, the extra-framework cations, can include any metal (or small molecular cation-former such as $NH_3$) capable of forming a crystalline aluminosilicate structure having the above empirical formula I. The symbol I| denotes that an integer number i of metal oxides are present in the formulation. The value of i may be from 1 up to the number of metals in the periodic table, for instance from 1 to as much as 40 or more, but more typically will be from 1 to 4, usually 1, 2 or 3, usually 2. It is likely that various metal cations will be present as natural impurities in the zeolite. The symbol x indicates the ratio of silica to alumina and y indicates the ratio of water to alumina in the composition (molar ratio). The symbol $z_i$ represents the proportion of each cationic moiety $M^i$ in proportion to alumina in the compound and $z_i$ will be from 0 to 1 with the constraint that, if stoichiometry is assumed, $\Sigma_j z_i$ should equal 1. If only alkali metal extra-framework cation is present in the structure, the formula can be written more simply as formula II:

$$M_2O.Al_2O_3.xSiO_2.yH_2O \qquad \text{II}$$

$M^i$, the extra-framework cations, can include any metal (or small molecular cation such as NH4) capable of forming a crystalline aluminosilicate structure having the above empirical formula I. $M^i$ may be or include an alkali metal such as sodium or potassium, in which case $n_i=1$ and $z_i=1$ to give stoichiometry. Typically, zeolites are available commercially as alkali metal zeolites, usually sodium zeolites or potassium zeolites. Other extra framework cations may be present in the commercial alkali metal zeolites as impurities at up to say 0.5 molar percent of the extra-framework cation.

The zeolites useful for the invention can have the structure of any of the known zeolites. The structure and characteristics of many zeolites are described in the standard work "Zeolite Molecular Sieves" by Donald W. Breck, published by Robert E, Krieger Publishing Company. Usually, the value of x in the above empirical formula is typically from 1.5 to 10. The value of y, which represents the amount of water contained in the voids of the zeolite, can vary widely. In anhydrous (dry) material y=0 and, in fully hydrated zeolites, y is typically up to 5.

Zeolites useful in this invention may be based on naturally-occurring or synthetic aluminosilicates and the preferred forms of zeolite have the structure known as zeolite P, zeolite X, zeolite Y or zeolite A. The zeolite may, for instance, be an alkali metal zeolite, or any other zeolite, including ion-exchanged zeolites as described herein. For reasons of suitability of channel size and for its capacity to carry high levels of releasably adsorbed nitric oxide, zeolite A is a preferred zeolite for use in carrying nitric oxide. Zeolite A typically has a value for x of about 2.

A single metal cation may be present as the extra-framework cation in the zeolite, or, as shown in formula II, a plurality of different extra-framework cations $M^i$ having valencies $n_i$ may be present. This can be represented by formula I above where the symbol I represents the number of different cations present in the zeolite. The value of i may be from 1 up to the number of metals in the periodic table, for instance from 1 to as much as 40 or more, but more typically will be from 1 to 4, usually 1, 2 or 3, usually 2. It is likely that various metal cations will be present as natural impurities in the zeolite.

Typically, ion-exchanged zeolites may be prepared by starting from an alkali or alkali earth metal zeolite, usually an alkali metal zeolite, and exchanging part or all of the alkali or alkali earth metal in the starting zeolite formulation with a different metal. For an alkali metal zeolite, this leads to a compound having the formula Ill:

$$w(M^i{}_{2/g}O).z(M_2O).Al_2O_3.xSiO_2.yH_2O \qquad \text{III}$$

Where M' is the exchanging metal, having a valency g from 1 to 6, typically from 1 to 3, M is an alkali metal of valency 1 (usually sodium), w is the molar proportion of exchanging metal oxide in the formula, and assuming stoichiometry should have a value from 0 to 1, z is the molar proportion of alkali metal oxide remaining after exchange, and should have a value from 1 to 0 (0 signifying total exchange). The symbol x is the molar proportion of silica and y the molar proportion of water (all in ratio to the amount of aluminium oxide). The values for x and y are as set out hereinbefore, and Equation III can be seen to correspond to equation I in form. A corresponding formula can easily be derived for an alkali earth metal zeolite, with (MO) replacing ($M_2O$) in formula III.

Methods for carrying out such ion exchange are well known in the art. Typically, the starting (e.g. sodium or other alkali metal) zeolite is contacted with an aqueous solution of a metal salt with which exchange is required. A soluble salt such as an acetate may be used. Following such exchange, in theory the resulting ion-exchanged zeolite should have a formula with (w+z=1) in order to provide stoichiometry. We have found experimentally that for compounds formed by such ion exchange, depending upon the ion exchange conditions used, w may be greater than 1-z in some cases for the ion-exchanged compounds formed, in other words with an excess of oxide of M' present in the resulting exchanged compound. Such ion-exchanged zeolite compounds are included by the term zeolite as used in this specification, even though they may include an excess of exchanging metal oxide over the amount required by stoichiometry. Without wishing to be bound by theory, we believe that the excess of exchanging metal oxide may arise from co-precipitation of the insoluble oxide of the exchanging metal. For a fully ion-exchanged zeolite, z will be zero with w being 1 or more, depending upon the ion-exchange method employed.

In ion-exchanged zeolites as described above, more than one exchanging metal may be used, either sequentially or simultaneously, to form the ion exchanged zeolite from an alkali metal or alkali earth metal zeolite. The starting zeolite may, for instance, contain both alkali earth (valency 2) and alkali (valency 1) metals as extra-framework cations, as well as optionally other metals. The starting zeolite is preferably an alkali metal zeolite having an extra-framework cation consisting essentially of an alkali metal. By consisting essentially it is meant that the value of $z_j$ summed for the alkali metal oxides in formula I is 0.95 or more.

The zeolites have been found to be capable of adsorbing nitric oxide into the pores and channels, which their structure contains, and which makes them effective as ion-exchanging materials. This is described in detail in WO 2005/003032.

It has been found that the binding of the nitric oxide within the zeolite channels is particularly strong when the extra-framework cations present within the zeolite include alkaline earth metals such as Ca or Mg, or one or more transition metals. The presence of such a transition metal in the zeolite is preferred. In this specification, by "transition metals" is meant the 40 chemical elements 21 to 30, 39 to 48, 71 to 80 and 103 to 112 (i.e. zinc is included in the term transition metal even though its d-shell has a $d^{10}$ configuration).

Suitably, the amount of transition metal cation is such that the value of z for a non-transition metal cation (e.g. alkali earth metal or alkali metal M) in formula III above is less than 0.95, preferably less than 0.8, more preferably less than 0.5. For instance, an ion-exchanged alkali metal zeolite with 5 molar % or more of the alkali metal exchanged by transition metal cation(s) may be used, preferably 20 molar % or more, even more preferably 50 molar % or more of the alkali metal is exchanged. Suitably 30 molar % or more, preferably 40 molar % or more, even more preferably 50 molar % or more of the extra framework cation of the zeolite particles is a transition metal cation. For instance, an ion-exchanged alkali metal zeolite with a Percent Exchange (PE) of 30% or more, preferably 40% or more, even more preferably 50% or more, for the transition metal cation may be used, using the PE as defined above. Particularly suitable transition metals include Co, Ni, Zn, Fe, Cu, Mn and Ag and mixtures thereof. The transition metal cation is preferably Cu, Zn, Ag or a mixture thereof. Zn is a particularly preferred transition metal cation for use as an extra-framework cation in zeolites to be used for carrying nitric oxide in the compositions of the invention. This is because of its antipathogenic effects, its ready availability and its low toxicity.

The tetrahedral co-ordination of alumina and silica gives a negative framework to the structure of the zeolite and the extra framework cations balance the negative charge. Thus to be stoichiometric, for every mole of $Al_2O_3$ in formula III, one mole of $M_2O$ is required to provide charge balance. If the alkali metal is exchanged by another cation, as shown in Formula I the combined charge should be 1 if the ion exchange is to be considered as stoichiometric. Percent Exchange (PE) as defined in this specification can be determined using the following simple Equation:

Percent Exchange=$(1-z) \times 100$, where z is as defined by Formula III. In other words the percent exchange (PE) by transition metal cation is suitably 5% or more, preferably 20%, or more, more preferably 50% or more.

It is particularly preferred for the invention to use a zeolite comprising an antipathogenic (e.g. antimicrobial, antiviral or antifungal) transition metal cation as an extra framework metal cation providing positive charge. The antipathogenic cation is suitably Cu, Zn, Ag or a mixture thereof. Such antipathogenic cations may become active upon wetting of the dressing composition, allowing them to exchange with ions in the fluid wetting the dressing. Zn is a particularly preferred antipathogenic metal cation for use as an extra-framework cation in zeolites to be used in the compositions of the first aspect of the invention because of its ready availability and its low toxicity. It is also highly effective for assisting the zeolite to releasably adsorb nitric oxide. Preferably, the zeolite comprises an antipathogenic metal cation as an extra framework metal cation providing positive charge. Suitably, an ion-exchanged alkali or alkaline earth metal zeolite with 5 molar % or more, preferably 20 molar % or more even more preferably 50 molar % or more of the alkali or alkaline earth metal exchanged by antipathogenic (for instance antimicrobial, antiviral or antifungal) metal cation(s) may be used. By this it is meant that z in formula III above is suitably less than 0.95, preferably less than 0.8, more preferably less than 0.5, where M' is one or more antipathogenic cations replacing the alkali metal in the composition. The antipathogenic metal cation is preferably the transition metal cation of the zeolite compound.

When a number of different metal cations are present in an ion exchanged zeolite in addition to the exchanged alkaline earth or alkali metal cation, and the resulting ion-exchanged zeolite compound has an excess over stoichiometry of exchanging metal oxide, it is to be assumed that the exchanging cations exchange with the alkali or alkaline earth metal of the original zeolite in proportion to their molar proportions in the final ion-exchanged compound.

In ion-exchanged zeolites as described above, more than one exchanging metal may be used, either sequentially or simultaneously, to form the ion exchanged zeolite from an alkali metal zeolite or alkali earth metal zeolite. The starting zeolite may contain both alkali earth (valency 2) and alkali (valency 1) metals as extra-framework cations, as well as optionally other metals (for instance as impurities or intentionally present.

It has been found that a surprising increase in gas adsorption capacity can be achieved for ion-exchanged zeolites prepared from alkali metal zeolites by modifying the exchange process in order to reduce the excess of exchanged extra-framework metal oxide.

A first method for preparing a second zeolite compound, suitable for use as a zeolite comprising releasably adsorbed nitric oxide for use in the various aspects of the invention has been found, The first method is a method for preparing a second zeolite compound comprising a non-alkali metal selected from the group consisting of group II metals, group III metals and transition metals and mixtures thereof, as an extra-framework cation, from a first zeolite compound by ion exchange.

The first method comprises the steps:

a) providing a first zeolite compound having an extra-framework cation consisting essentially of an alkali metal and wherein x, the ratio SiC^/A^Oa for the first zeolite is from 1.5 to 10, b) preparing a aqueous slurry of the first zeolite having a pH and adjusting the pH of the slurry to a pH from 3 to 9, c) mixing the aqueous slurry and an aqueous solution of the non-alkali metal whereby the second zeolite compound comprising the non-alkali metal is formed.

This method may provide a second, ion-exchanged zeolite compound represented by the formula III as set out previously:

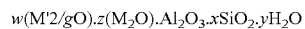  III wherein M' is a non-alkali metal selected from the group consisting of group II metals, group III metals and transition metals and mixtures thereof, having a valency g from 1 to 6, preferably 1 to 3, M is an alkali metal of valency 1, w is the molar ratio of non-alkali metal oxide to $Al_2O_3$ and is greater than 0 and up to 1.15, z is the molar ratio of alkali metal oxide to $Al_2O_3$ and has a value from 0 to 0.7, x is the molar ratio of $SiO_2$ to $Al_2O_3$ and is from 1.5 to 10 and y is the molar ratio of water to $Al_2O_3$ and is from 0 to 12, and wherein w+z is from 0.8 to 1.15, preferably from 0.9 to 1.10, more preferably from 0.95 to 1.05.

Without wishing to be bound by theory, it is hypothesised that aqueous slurries of zeolites, particularly alkali metal zeolites, particularly those having x=10 or less tend to have an alkaline pH, often greater than 10. It is believed that this high pH may result in the undesired precipitation of insoluble salts as metal cation exchange proceeds, leading to deposits of metal oxide on the resulting exchanged zeolite particles. For a fully exchanged zeolite, this would result in z=0 and w greater than 1.

It is believed that the use of the first method as set out above deters excessive precipitation of exchanging metal oxide so that the resulting second, ion-exchanged zeolite compound has w+z closer to 1 than for the prior art.

By "aqueous" as applied to a solution or slurry or dispersion is meant that the liquid from which the solution, slurry or dispersion is prepared comprises at least 60%, preferably at least 80% by weight of water.

Suitably, the alkali metal of the first zeolite, used as starting material in the first method, is sodium, potassium or a mixture thereof, preferably sodium. Preferably, $x=SiO_2/Al_2O_3$ for the first zeolites, is 5 or less, more preferably 3 or less. For instance, the first zeolite particles may be of zeolite A, for which x is about 2.

In step (b) of the first method the pH of the slurry is adjusted to a pH from 3 to 9, preferably from 4 to 8, more preferably from 5 to 7. If the pH is too low, excessive dissolution of the first zeolite may occur, leading to loss of the desired zeolitic channel structures. Any suitable acid may be used to adjust the pH, with mineral acids such as sulphuric, nitric or hydrochloric acid being preferred. Mixtures of acids may be used.

Conventional slurry ion exchange of an alkali metal zeolite such that z is 0.7 or less, without the pH reduction step (b) of the first method, typically yields values of (w+z) greater than 1.15. Suitably z is 0.7 or less, preferably 0.6 or less, more preferably 0.5 or less, even more preferably 0.4 or less, such that the second zeolite compound may have a high capacity for releasable adsorption of gas, particularly nitric oxide. The first method may even yield values of (w+z) which are less than 1. Without being bound by theory, it is thought that values less than one may arise from alkali metal being partially exchanged by protons in addition to being predominantly exchanged by the non-alkali metal cation(s).

The second or ion-exchanged zeolite compound prepared by the above first method, particularly when zinc is used as an extra-framework cation, is suitable for carrying releasably adsorbed nitric oxide for use in the various aspects of the invention, and may comprise at least 0.5, preferably at least 0.9, more preferably at least 1.5 mmol/g even more preferably at least 2.0 mmol/g of releasably adsorbed nitric oxide.

The particle diameter of the zeolite or zeolites used in the compositions of this invention may be adjusted to suit the intended use in a dressing. Typically, the volume mean particle diameter will be from 0.1 fjm to 20 pm. More preferably, the zeolite will have a volume mean particle diameter from 0.5 to 10 pm. More preferably, the zeolite will have a volume mean particle diameter from 1 to 5 pm. However, the zeolite particles may also be in granular form, the granules or beads being made up of agglomerated zeolite particles of the above suitable or preferred sizes. The zeolite is suitably present as particles, beads or granules dispersed substantially uniformly throughout the dressing of the invention.

The volume mean particle diameter of the zeolite particles may be determined by laser diffraction using a Malvern Mastersizer® model S, with a 300 RF lens (measurement range 0.05-3480 pm), Malvern Mastersizer® software v 2.18 and a DIF 2012 dispersion unit. This instrument, made by Malvern Instruments, Malvern, Worcestershire, utilises Mie theory to calculate the particle size distribution. Mie theory predicts how light is scattered by spherical particles and takes into account the refractive index of the particles. The real value used for the zeolite refractive index is 1.5295 and 0.1 for the imaginary refractive index (absorption of light), with water dispersant at 1.33 refractive index.

Before measurement, the sample is dispersed ultrasonically in water for 2.5 minutes on a 50% power setting to form an aqueous suspension. The pump speed i.e. the speed at which the dispersed sample is passed through the instrument, is set at 50% (1250+/−20 r.p.m.) The stirrer speed i.e. the speed at which the zeolite particles are stirred within the disperser unit, is set at 50% (530+/−5 r.p.m.). Low power 2-5 mW He/Ne laser light (wavelength 632.6 nm) is passed through a flow cell containing the particles dispersed in de-ionised water. The scattered light intensity is measured as a function of angle and this data is used to calculate an apparent particle size distribution. The volume mean particle diameter are easily obtained from the data generated by the instrument.

The amount of zeolite, expressed as weight of zeolite present in the composition is suitably from 0.4 or 0.5 to 70% by weight, preferably from 5 to 60%, more preferably from 10 to 50% by weight of the overall composition. The weight of zeolite as expressed herein includes any moisture or other compounds such as gases held within the zeolite (for instance within in pores or channels).

Although hydrated zeolites may be utilised in the compositions of the invention, preferably, the zeolite is a dry zeolite. For the purposes of this specification, dry zeolite is considered to be zeolite, which has been treated to remove substantially all physisorbed (i.e. constitutional) water. Suitably, dry zeolite comprises less than 1% by weight physisorbed water, preferably less than 0.5%, more preferably less than 0.1%. For instance, the zeolite may have been heated at 300° C. under vacuum to constant weight to remove physisorbed water. It may well be that bound water is also present within the zeolite which cannot be removed by heating to 300° C. under vacuum to constant weight. The use of a dry or dehydrated zeolite gives the benefit that the dressing composition has additional water absorbency arising from uptake of moisture to form a hydrated zeolite. For instance, dry zeolite A may have the capacity to take up 20% by weight of its dry weight as water. Generally, the hydration of zeolite is an exothermic reaction and the heat generated by this reaction as a dressing comprising a dehydrated or dry zeolite takes up liquid may be beneficial to the wound healing process or to provide a sensory cue to the patient of the effectiveness of the dressing containing the dressing composition.

The preparation of zeolites containing releasably adsorbed nitric oxide is set out in the published patent application WO 2005/003032. Zeolites are also capable of releasably adsorbing gases such as nitric oxide ammonia, hydrogen sulphide, carbon monoxide, carbon dioxide, sulphur dioxide, oxygen, formaldehyde, etc. Zeolites have been used in the prior art for odour prevention, for instance in public toilets, horse stables, chicken houses, litter trays by adsorbing offensive ammonia fumes.

The zeolite in the compositions of the invention may also provide the advantage of adsorbing undesirable odours, for instance from wounds, and may also be used for the releasable adsorption of other medically useful gases.

Prior to loading a zeolite with adsorbed nitric oxide, the zeolite is suitably fully or partly dried, preferably fully dried as detailed above, in order to remove water from the zeolite channels. Loading of the zeolite with the nitric oxide may be performed with pure NO, or with NO included in a carrier gas such as an inert gas (e.g. helium, or argon) or a non-reactive gas such as nitrogen. For industrial manufacturing purposes, nitrogen is a preferred, non-reactive gas. Details for a suitable process for loading NO into a zeolite are described in WO 2005/003032. Suitably, loading with NO is carried out under a pressure from 1 to 10 bars, 1 bar being typical atmospheric pressure.

Suitably, the zeolite used in the dressing composition of the invention comprises at least 0.2 mmol/g, preferably at least 0.5 mmol/g, even more preferably at least 0.9 mmol/g or 1.0 mmol/g of releasably adsorbed nitric oxide. If the zeolite is a second zeolite as prepared by the first method set out hereinbefore, higher levels of releasably absorbed nitric oxide may be present, such as at least 1.5 mmol·g or at least 2.0 mmol/g.

Upon exposure of the nitric oxide loaded zeolite to water, for example from an aqueous environment such as sweat or blood, the nitric oxide is displaced from its binding site within the zeolite resulting in release of nitric oxide gas into the surroundings of the zeolite from the dressing composition of the invention.

The dressing composition of the first aspect of the invention comprises an elastomeric adhesive composition in addition to the zeolite comprising releasably adsorbed nitric oxide. Suitably, the composition of the first aspect of the invention comprises from 99.5 to 30% by weight of an elastomeric adhesive composition, preferably from 95 to 40% by weight, even more preferably from 90 to 50% by weight.

Preferably, the dressing composition consists essentially of, or is formed from, a zeolite comprising releasably adsorbed NO and an elastomeric adhesive composition.

Without being bound by theory, it is thought that the combination of hydrocolloid-adhesive composition and NO-releasing zeolite is particularly effective because the elastomeric adhesive composition mediates the transport of body fluids (such as sweat, wound exudate, etc.) from the skin to the zeolite, allowing for gradual release of NO originally adsorbed in the zeolite as the zeolite interacts with the proton donor (water) in the body fluids. Furthermore, the structural integrity (i.e. mechanical strength and resistance to deformation when stressed) of the composition of the invention means that it is less prone to being applied as a smeared or flattened layer, such as would typically be used if the NO-releasing zeolite were contained within a cream or an ointment. It has now been found that such smeared or flat layers tend to release high levels of NO immediately after application, exhausting the potential supply for prolonged delivery of the NO.

Elastomeric adhesive compositions, particularly hydrocolloid-adhesive compositions are known in the art as dressing compositions for use as components of dressings, in particular dressings used for covering wounds in order to prevent exposure of a wound to external contamination.

Elastomeric adhesive compositions are well known in the art. The elastomeric adhesive composition of the Invention suitably comprises a rubbery elastomer and optionally a hydrocolloid. Although elastomeric adhesive compositions comprising a hydrocolloid are preferred (i.e. hydrocolloid-adhesive compositions), it has surprisingly been found that zeolite can replace hydrocolloid entirely in an elastomeric dressing composition.

Typical hydrocolloid-adhesive compositions comprise an elastomeric polymer such as polyisobutylene, in combination with one or more water-soluble or water-swellable hydrocolloids. Suitable hydrocolloids known and used in the art include pectin, gelatine, carboxymethylcellulose and mixtures thereof.

When included in a wound dressing or in an ostomy seal, the elastomeric adhesive composition is usually laminated onto a polymeric carrier film, which may be water-permeable or water impermeable and the elastomeric adhesive composition may be applied directly onto the skin.

A problem with many conventional hydrocolloid-adhesive compositions used in dressings is their susceptibility to breakdown upon exposure to wound exudate and body fluids (i.e. the hydrocolloid-adhesive compositions tend to lose structural integrity upon hydration). Some absorption of fluid by the hydrocolloid-adhesive composition is desirable, but excessive swelling of the composition may lead to loss of integrity and the composition may lose its moisture seal with the skin. This may lead to leakage and a need to replace the dressing comprising the hydrocolloid-adhesive composition more frequently. A surprising benefit for the dressing compositions of the invention is that the incorporation of zeolite comprising releasably adsorbed nitric oxide additionally provides the benefit of helping the elastomeric adhesive or hydrocolloid-adhesive composition to maintain its integrity when fully swollen by liquids such as water or body fluids.

The elastomeric adhesive composition of the invention suitably comprises a rubbery elastomer and optionally a hydrocolloid. Materials for forming the rubbery elastomeric adhesive matrix of an elastomeric adhesive composition are well known in the art and described, for example, in U.S. Pat. Nos. 3,339,546 and 4,253,460. Both natural or synthetic rubber or mixtures thereof are useful, also Kratons® (block copolymers of styrene/butadiene and the like available from Shell Chemical Company), polybutene (e.g. polyisobutylene) and polyacrylates may be used. Tackifiers, plasticizers and other materials known in the art for incorporation in the rubbery elastomeric matrix may also be used (See, for example, U.S. Pat. Nos. 4,231,369 and 4,551,490).

Polyisobutylene is particularly useful as the rubbery elastomeric matrix. Preferably, the polyisobutylene to be used is a mixture of low molecular weight polyisobutylene (viscosity average molecular weight of about 10,000 to 12,000) and a higher molecular weight polyisobutylene (viscosity average molecular weight of about 80,000 to 100,000) in a ratio of about four to one. Suitable low and high molecular weight polyisobutylene pressure sensitive adhesives are available from Exxon Chemical Company under the tradenames Vistanex® LM and Vistanex® L-100, respectively.

The elastomeric adhesive composition may comprise any suitable level of rubbery elastomer, for instance from 15 to 100 percent by weight of elastomer expressed by weight of the elastomeric adhesive composition. When the elastomer is present in amounts below about 35 percent, the composition tends to exhibit low adhesive properties. For wound dressing applications, it is desirable to minimize the amount of elastomer present, consistent with achieving adequate adhesive properties, in order to maximize the level of hydrocolloid, thereby achieving maximum fluid absorbency. Where high adhesion is needed, higher levels of elastomer may be used.

Suitable elastomers are disclosed, for instance, in EP-A-1 159 972.

The elastomeric adhesive composition optionally and preferably includes a hydrocolloid, typically comprising from 0 to 85 percent by weight of the elastomeric adhesive composition. A hydrocolloid is a substance which forms a gel with water or aqueous liquids, swelling as it takes up the liquid.

The hydrocolloid for use in the present invention may be synthetically prepared or naturally occurring. Varieties of hydrocolloids within the scope of the present invention include synthetic polymers prepared from single or multiple monomers, naturally occurring hydrophilic polymers or chemically modified naturally occurring hydrophilic polymers.

Examples of such hydrocolloids include polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccharides, alginates, xanthan gums, guar gums, and cellulosic polymers. Suitable hydrocolloids include synthetic polymers that may be either linear or cross-linked.

The hydrocolloid is suitably dermatologically acceptable and non-reactive with the skin of the subject (or with other components of the composition of the invention).

Particularly suitable hydrocolloids are water soluble or swellable hydrocolloids chosen from the group consisting of polyvinyl alcohols, powdered pectin, gelatin, methyl cellulose, hydroxypropyl methyl cellulose, carboxymethylcellulose, hydroxypropyl cellulose and mixtures thereof. A particularly suitable hydrocolloid is carboxymethylcellulose (CMC).

Preferably, the composition according to the first aspect of the invention comprises a hydrocolloid-adhesive composition wherein the hydrocolloid adhesive composition comprises, by weigh of the hydrocolloid-adhesive composition, from 15 to 70% of a hydrocolloid and from 30 to 85% of an elastomer.

In addition to the elastomer and optionally the hydrocolloid, the elastomeric adhesive composition may also further comprise a hydrocarbon resin tackifier. This may be present as up to 60 by weight of the hydrocolloid-adhesive composition. Suitable hydrocarbon tackifiers are also disclosed in EP-A-1 159 972.

The elastomeric-adhesive composition may further comprise up to 60% by weight of a non-polar oily extender.

Preferably, the elastomeric adhesive composition suitably comprises less than 5% by weight of water, preferably less than 2.5%, more preferably less than 1% of water.

The dressing composition of the invention may be particularly useful for treatment of, wounds, particularly chronic wounds, particularly on diabetic or elderly patients where wound healing is well-known to be problematic. The compositions of the invention may be useful in bandages, or for topical application as the composition as such (which may then, for instance, be covered by a protective layer to form a dressing).

The composition may further comprise an additional pharmaceutically active agent. The choice of agent may depend upon the purpose to which the dressing composition is to be put. For instance, for the treatment of chronic wounds, the dressing may include a wound-treatment agent such as becaplermin (sold under the trade name Regranex®).

Compositions of the invention may be prepared in a straightforward manner by dispersion of the NO-carrying zeolite into the elastomeric adhesive composition used standard blending equipment. For instance, a z-blade mixer (Supplied by Winkworth Machinery Limited Ltd.) may be used to prepare compositions of the invention.

Compositions of the present invention may be applied for use as a dressing to the skin or to other accessible surfaces of the body, such as the interior of the mouth, vagina, rectum etc. The compositions are suitable for both human and veterinary use.

The nitric oxide delivered from a dressing may also act as vasodilator and so may be used in prevention of erectile dysfunction, treatment of anorgasmia, enhancement of transdermal drug delivery, vasodilatation prior to surgical insertion and the like. Nitric oxide may also act as a skin pigment modifier.

Further uses of the dressing composition, in addition to use in wound treatment dressings, include various applications where the dressing may be used to apply nitric oxide, and optionally including one or more additional pharmaceutically active agents, to the skin or to body cavities;

- Use for treatment of wounds, or for application of an agent for treatment of wounds, particularly for improving wound-healing rate, particularly in the elderly or in diabetic patients, particularly for chronic wounds.
- Use for treatment of infections of the skin. The dressing may be used to keep a pharmaceutical treatment agent in contact with the skin, and in such uses the zeolite preferably comprises an antipathogenic extra-framework cation. The nitric oxide will be released by moisture from sweat from the skin contacting the NO-carrying zeolite by diffusion through the hydrocolloid-adhesive composition.
- Use for application of composition comprising nitric oxide, to act as a vasodilator, to the skin of genitalia for treatment of sexually related dysfunction such as erectile dysfunction or anorgasmia, or for vasodilation of subcutaneous tissue prior to insertion of an invasive device such as a catheter, vascular access device, needle, syringe or the like.
- Use for treatment or application to the skin of an agent for treatment of neuropathy.
- Use for skin pigment modification or application to the skin of a pigment modifier.
- Use for treatment of fungal infections or for application to the skin of an agent for treatment of fungal infections.
- Use for inhibition of inflammation or application to skin of an agent to inhibit inflammation.
- Use for treatment of skin disease such as eczema, psoriasis, dermatitis, melanoma and the like, or for application of an agent to treat such skin diseases.
- Use for application to the skin of a pharmaceutically active compound to be transdermally absorbed into the bloodstream of a patient.
- Use in an ostomy dressing or seal For all of the above-mentioned uses of the dressing composition, the zeolite preferably comprises an antipathogenic extra-framework cation. Nitric oxide may be released by moisture from sweat from the skin. For some applications, the nitric oxide and/or the antipathogenic extra-framework metal cation, when present, may act as the active agent for treatment, or may enhance the activity of an active agent applied by means of the dressing composition, for instance by the nitric oxide increasing blood flow in the skin in the vicinity of the dressing composition such that transdermal uptake of the active agent is enhanced as the active agent and nitric oxide are gradually released together.

Further aspects of the invention include methods of treatment on the human body (or animal body where appropriate) employing a composition according to the first aspect of the invention for the medical uses detailed above.

The second aspect of the invention provides a dressing for application to skin comprising a backing layer, for instance a film of water-impermeable polymer such as polyurethane, holding a dressing layer comprising a skin contacting surface and a dressing composition according to the first aspect of the invention. The dressing may further comprise a release sheet or liner, such as sheet, for instance, of a silicone paper, removably attached to the skin-contacting surface of the dressing layer. The dressing of the second aspect of the invention may be a self-adhesive dressing or may need to be held to the skin by some other means such as a bandage or dressing cover.

The backing layer may suitably be a non-permeable backing layer in order to prevent undesired loss of nitric oxide. The dressing composition may be directly adhered to the backing layer, or where the backing layer has a foam structure, the dressing composition may be partially or entirely enclosed within a void space of the backing layer. A suitable foam structure may have a solid matrix of a flexible resilient material such as a polymer, e.g. polyurethane, having an interconnected void space of pores held therein. Such foam or sponge layers are well known for use in dressings.

The preferred features of the composition of the first aspect of the invention may be used individually or In combination for the second aspect of the invention. For instance, the zeolite may include an antipathogenic metal ion, such as Cu, Ag or Zn, preferably Zn, as an extra-framework metal cation.

Zeolite, as set out hereinbefore but with or without releasably absorbed nitric oxide, may be of use in a first further composition. The first further composition provides a dressing composition comprising from 4 to 70% by weight of zeolite and 96 to 30% by weight of elastomeric-adhesive composition. The effect of the zeolite is to improve the integrity of the dressing composition integrity after uptake of body fluids by the dressing composition. Although the zeolite is preferably an NO-releasing zeolite, as detailed hereinbefore, this is not essential in order to obtain improved integrity for such dressing compositions when swollen by liquids such as water or body fluids. The elastomeric adhesive composition is suitably a hydrocolloid-adhesive composition wherein the hydrocolloid adhesive composition comprises, by weigh of the hydrocolloid-adhesive composition, from 15 to 70% of a hydrocolloid and from 30 to 85% of an elastomer. Other features and uses of the various aspects of the invention set out hereinbefore, are also applicable, where appropriate, to the first further composition.

The zeolites containing releasably absorbed nitric oxide, as set out hereinbefore, may also be used in a second further composition. The second further composition provides a solid composition comprising a solid polymeric material with zeolite particles dispersed therein, wherein the zeolite particles comprise releasably adsorbed nitric oxide. Suitably, the solid composition has a foam structure wherein the solid polymeric material with zeolite particles dispersed therein forms a continuous solid phase of the foam structure. The zeolite particles are NO-releasing zeolite particles as set out hereinbefore.

The solid polymer used in the solid compositions of this disclosure may be any suitable polymer, natural or synthetic.

For instance, the polymer may be a thermosetting or a thermoplastic polymer resin or a natural or synthetic rubber.

Suitable thermoplastic polymers for the second further composition include polyvinyl chloride) and co-polymers thereof, polyamides and co-polymers thereof, polyolefins and co-polymers thereof, polystyrenes and co-polymers thereof, poly(vinylidene fluoride) and co-polymers thereof, acrylonitrilebutadiene-styrene, polyoxymethylene and acetal derivatives, polybutylene terephthalate and glycolised derivatives, polyethylene terephthalate and glycolised derivatives, polyacrylamide nylon (preferably nylon 11 or 12), polyacrylonitrile and co-polymers thereof, polycarbonate and co-polymers thereof. Polyethylene and polypropylene, which may be modified by grafting of carboxylic acid or anhydride groups onto the polymer backbone, are suitable polyolefins. Low density polyethylene may be used. A polyvinyl chloride) may be plasticised, and preferably is a homopolymer of vinyl chloride.

Examples of thermosetting polymers which may be used for the second further composition are epoxy resins, polyester resins, hybrid epoxy-polyester resins, polyurethane resins and polyacrylic resins.

Natural polymers such as collagen materials may also be used as solid polymers for the second further composition, as may synthetic or natural rubbers. Suitably, the solid polymeric material is selected from the group consisting of thermoplastic polymers and thermosetting resins.

Commonly used methods may be employed for dispersing the zeolite throughout the solid polymer, for instance melt-mixing or dry blending followed by melting.

A preferred polymer is polyurethane, particularly elastic, crosslinked polyurethanes (for instance as described in WO 97/43328).

The polyurethane may be prepared by customary processes, as described, for example, in Becker/Braun, Kunststoff-Handbuch, Vol. 7, Polyurethane, p. 121 ff., Carl-Hanser, 1983.

Polyurethanes have good skin compatibility and also oxygen and water vapour permeability. Aliphatic polyester urethanes have proven particularly useful for wound dressings.

The zeolite particles, comprising releasably adsorbed nitric oxide, may be incorporated into polyurethanes by admixing the zeolite to the polyurethane base materials without disrupting the polyurethane reaction, and they are able to release nitric oxide despite incorporation into the polymer.

Suitably, the solid composition of the second further composition has a foam structure wherein the solid polymeric material with zeolite particles dispersed therein forms the continuous solid phase of the foam structure.

The foaming of polymers for use in dressings is well known in the art, and such foamed polymers are particularly useful for this invention, with the polymer solid making up the continuous solid phase of the foam structure, and enclosing a void space through which liquid can flow and be absorbed. As the zeolite particles are dispersed throughout the solid polymer and so contact and diffusion of liquid to the zeolite particles is facilitated, leading to release of nitric oxide from the zeolite particles and its diffusion and dissolution into the liquid. When such a foam is used as a dressing, liquid from the skin or a wound thus acts to release nitric oxide which may then diffuse back to the skin or wound through the liquid.

Polyurethanes are particularly preferred as polymers for such foams.

Preferably, the solid composition of the second further composition consists essentially of, or is formed from, a zeolite comprising releasably adsorbed NO and a solid polymer.

Without being bound by theory, it is thought that the combination of solid polymer and NO-releasing zeolite is particularly effective because the solid polymer mediates the transport of body fluids (such as sweat, wound exudate, etc.) from the skin or body to the zeolite, allowing for gradual release of NO originally adsorbed in the zeolite as the zeolite interacts with water from the body fluids.

When included in a topical dressing or in an ostomy seal, the second further composition may be formed into a film, which may be water-permeable or water impermeable and may be applied directly onto the skin or body orifice or wound, or may be laminated to other dressing layers which are directly applied to the body.

The solid polymer used in the second further composition is suitably dermatologically acceptable and non-reactive with the skin of the subject (or with other components of the composition of the invention).

The solid composition of the second further composition is particularly useful for use in dressings for treatment of chronic wounds, particularly on diabetic or elderly patients where wound healing is well-known to be problematic and where endogenous nitric oxide is known to be effective for speeding healing.

The solid composition of the second further composition may further comprise an additional pharmaceutically active agent dispersed within the solid polymer. The choice of agent may depend upon the purpose to which the solid composition is to be put. For instance, for the prevention of restenosis for a stent, the solid composition may comprise a restenosis prevention agent such as taxol, which may be eluted from the solid composition. For improving wound treatment, the additional agent may be a wound-treatment agent.

Solid compositions of the second further composition may used in a dressing applied to the skin or to other accessible surfaces of the body, such as the interior of the mouth, vagina, rectum etc. The compositions are suitable for both human and veterinary use.

The nitric oxide delivered from a dressing may also act as vasodilator and so may be used in prevention of erectile dysfunction, treatment of anorgasmia, enhancement of transdermal drug delivery, vasodilatation prior to surgical insertion and the like. The solid polymer composition of the second further composition may be used in order to form a condom from which NO may be delivered transdermally.

The second further composition may be a medical implant (i.e. an article for placement inside the human or animal body, such as a stent or a catheter or a pacemaker device, for instance) comprising a surface coating of a solid composition according to the first aspect of the invention. The slow release of NO from the surface coating may act to inhibit inflammatory reactions and scar formation, and in the case of a stent may inhibit restenosis.

Methods of treatment on the human body (or animal body where appropriate) employing a solid composition according to the second further composition may be carried out for the uses detailed hereinbefore.

An embodiment of a foamed solid composition according to the second further composition has a foamed polyurethane prepared according to the method of Becker/Braun, Kunststoff-Handbuch, Vol. 7, Polyurethane, p. 121 ff., Carl-Hanser, 1983, but comprising 20% by weight of the NO-loaded zeolite of Example 1 pre-dispersed into the liquid reagents prior to polymerisation and cross-linking to form polyurethane.

As an alternative preparation method, the Zeolite-NO of Example 1, as set out above, but without loaded NO, may be used to prepare the polyurethane foam, with NO loaded into the zeolite after foaming, polymerisation and cross-linking have taken place.

EXAMPLES

Specific embodiments of the present invention will now be described, by way of example only.

Example 1

A zinc ion-exchanged zeolite was prepared by slurrying 40 g of a commercial sodium zeolite A (zeolite Doucil 4A from PQ Silicas UK Ltd.—mean particle diameter typically 3 to 5 pm) in 4 litres of 0.05 molar zinc acetate solution for 24 hours. The resulting ion exchanged zeolite was filtered, washed with water and dried at 300° C. under vacuum for 3 hours.

Referring to formula IV, corresponding to formula III above but with M-Zn and hence g=2, M=Na, and with x=2 for zeolite 4A, y=0.

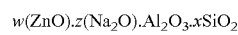

$$w(ZnO).z(Na_2O).Al_2O_3.xSiO_2 \qquad \text{IV}$$

the resulting zeolite as measured by XRF had w 0.65 and z=0.58.

The dry zeolite was loaded with nitric oxide by exposure to dry NO gas at a pressure of 2 bar at 25° C. Excess NO was allowed to escape and the NO loaded zeolite was flushed with a flow of dry nitrogen gas to remove any NO which was physisorbed rather than adsorbed.

NO levels were measure using a Sievers® NOA 280i chemiluminescence NO analyser. The NO was released by passing nitrogen gas of known humidity over the loaded zeolite in order to release the NO into the damp gas. The zeolite held about 0.95 mmol/g of releasably adsorbed NO. The material is referred to in these examples as "the Zeolite-NO".

Dressing compositions were prepared from polyisobutylene (PIB—polyisobutylene B12 SFN ex. BASF—as elastomer), and sodium carboxymethylcellulose (SCMC as the hydrocolloid—Blanose® 7H4FX as supplied by Hercules Ltd.), The compositions were prepared by dispersion of 40 parts by weight of the NO-loaded zeolite 4A and 10 parts by weight of the SCMC powder into 50 parts by weight of the PIB at 80° C. using a 1 litre Winkworth Z-blade mixer.

Flat sheets of the dressing composition were prepared using a hydraulic press at a pressure of 10 tonnes at 80° C., compressing the composition initially between two sheets of silicone release paper and finally between a silicone release paper and a polyurethane backing film (Inspire 2204 from Exopack Ltd.) to make a dressing.

The resulting dressing was allowed to equilibrate with water at 37° C. for 24 hours and was found to maintain its integrity after water uptake. It had good fluid uptake and was also found to release the nitric oxide into the water.

Example 2

A homogeneous ointment was prepared from 6.6 grams of Zeolite-NO prepared as for Example 1 and 13.4 grams of Emulsifying Ointment (BP) supplied by Boots Company PLC (50% by weight white soft paraffin BP and 20% by weight liquid paraffin BP with 30% by weight emulsifying wax). The resulting ointment is referred to below as "Ointment A".

A hydrocolloid preparation was prepared from 5 grams of Blanose 7H4FX (Polyisobuthylene) and 1 gram of SCMC blended with 4 grams of the Zeolite-NO of Example 1 in a dry nitrogen atmosphere. The hydrocolloid preparation is referred to below as "Hydrocolloid B"

The rate of release of NO from samples of Ointment A and Hydrocolloid B levels were measured using a Sievers NOA 2801 chemiluminescence NO analyser. In each case, a sample of either 0.4 grams of Ointment A or 0.3 grams of Hydrocolloid B was placed in a sealed glass vial (internal volume 4.55 mls), so that in each case the amount of NO initially in the vial was approximately the same for Hydrocolloid B or for Ointment A. The NO was released by passing nitrogen gas of known humidity at a flow rate of 180 millilitres/minute over the samples in the vial order to release the NO into the damp gas. The case entered and left the vial through hypodermic needles passing through a septum seal of the vial. The gas was humidified by first passing it through water in a Dreschel bottle at 22°G.

Figure 2:
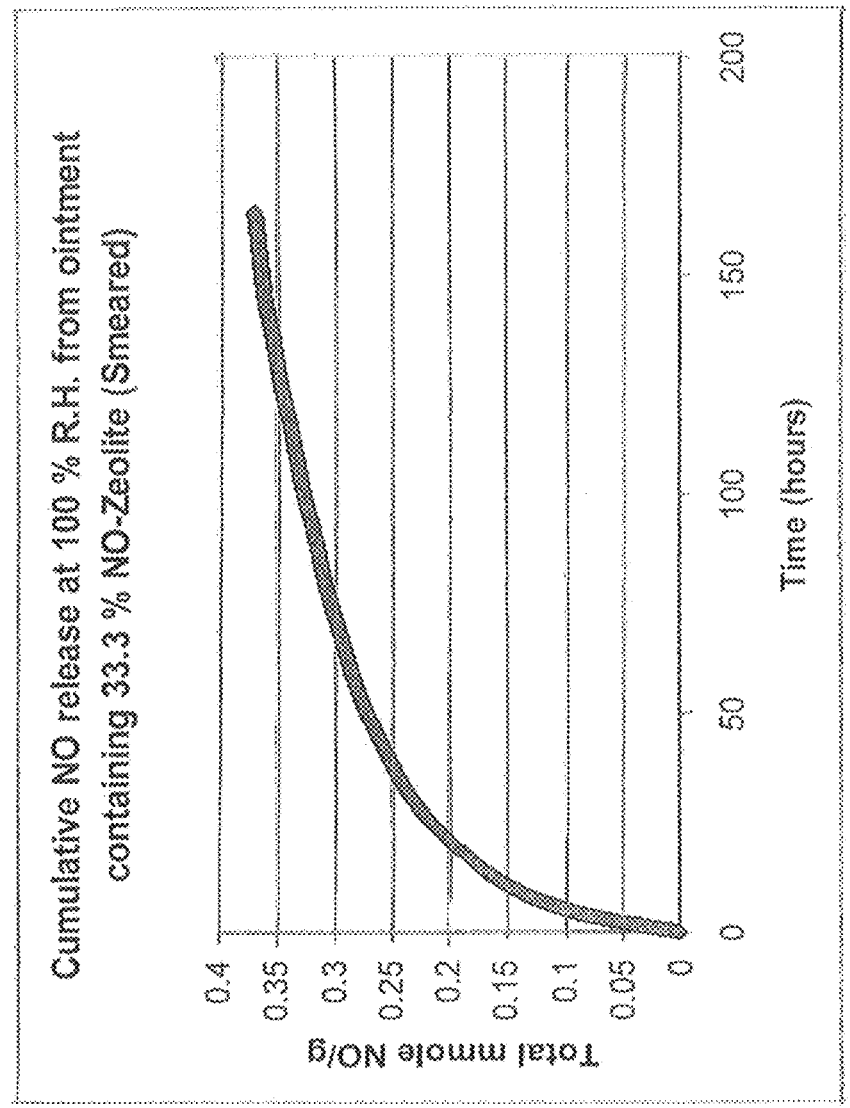
FIG. 2 is a graph showing the cumulative NO release (in mmol NO per gram of Zeolite-NO present in the sample) over time (in hours) at 100% relative humidity from a sample of Ointment A according to Example 2 where the ointment has been smeared to give a thin film.
Figure 3:
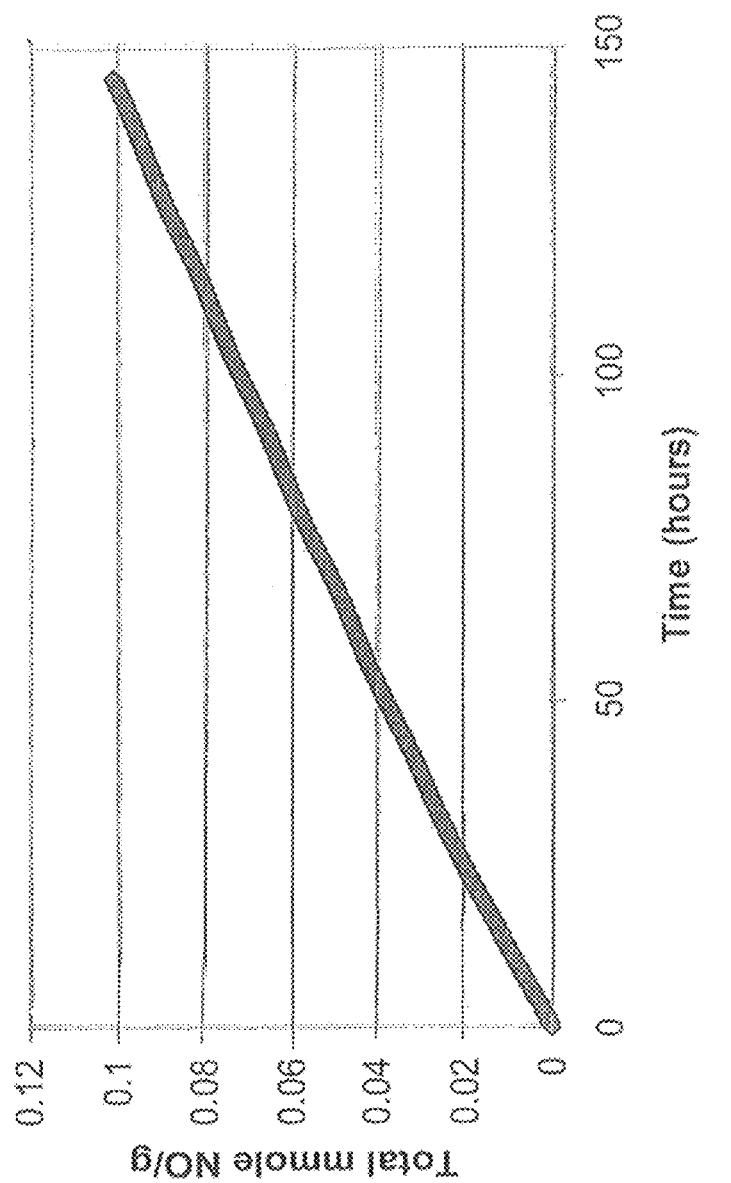
FIG. 3 is a graph showing the cumulative NO release (in mmol NO per gram of Zeolite-NO present in the sample) over time (in hours) at 100% relative humidity from a sample of Hydrocolloid B according to Example 2.

The results are shown in FIGS. 1 to 3.

Each Figure shows the total amount of NO released (in mmol NO per gram of Zeolite-NO present in the sample) as a function of time in hours. Total release would thus correspond to 0.95 mmol/g.

FIG. 1 shows the release from a non-smeared sample of Ointment A. This was present in the vial in a thick layer (about 1 mm thick) at the base of the vial, having the same surface area for release as the cross sectional area of the vial. After 150 hours, about 10% of the NO present in the sample has been released. The rate of release (expressed by the slope of the curve) is higher initially than it is at 150 hours. The rate of release falls gradually with time.

FIG. 2 shows the release from a sample of Ointment A where the ointment has been smeared to give a thin film (about 0.03 mm thick over the interior surface of the vial, so that release is from a greater surface area than for FIG. 1 (about 13 cm$^2$). For this case, about 35% of the NO present has been released by 150 hours, and the difference between the initial slope at zero time, and the final slope at 150 hours, is considerable. In other words, the rate of release falls markedly with time.

FIG. 3 shows the release from a sample of Hydrocolloid B having similar dimensions in the vial to the Ointment A sample of FIG. 1. In other words, the Hydrocolloid B sample is present as a thick layer (again about 1 mm thick) having the same surface area for release as the cross sectional area of the vial. The total amount of NO released by 150 hours is the same as for Ointment B in FIG. 1, but the rate of release, shown by the slope of the release curve, is constant over 150 hours.

Hence the data demonstrate that when contacted with a moist region so that release of NO is caused. The Hydrocolloid B shows a more uniform release behaviour than an ointment such as Ointment A when the release area is equivalent for the two samples.

In practice, the low structural integrity of an ointment will generally lead to it being present as a thin, smeared layer on the skin, and so a release profile such as that in FIG. 2 is more likely to be encountered. Compared to the behaviour of the Hydrocolloid B, release is highly non-uniform in rate and considerably more NO is released initially (with 10% released by 5 hours in FIG. 2, compared to 150 hours needed in FIG. 3).

The structural integrity of the hydrocolloid means that it can be maintained as a thick layer in a skin dressing, whereas it would be difficult to achieve such a thick layer with an ointment. Comparison of FIGS. 1 and 2 also shows that even if a thick layer of ointment was achievable, the hydrocolloid composition still has improved release rate uniformity Example 3

Zeolite 1

4 grams of zeolite 4A (Doucil® 4A from PQ Silicas UK Ltd.—mean particle diameter 3 to 5 pm) was slurried in 400 mls of 0.05M zinc acetate solution for 24 hours. The slurry was then filtered, washed and dried. The resultant product was analysed by XRF (x-ray fluorescence) analysis.

Zeolite 2 This example is as for Example A 1 but zinc sulphate was used as the soluble salt and a more concentrated solution and shorter exchange time were used. 22.5 grams of zinc sulphate heptahydrate was dissolved in 60 grams of deionised water. 13 grams of zeolite 4A was first slurried in 22.5 grams of deionised water. The pH of the slurry was 11.4. The zeolite slurry was then added to the zinc sulphate solution. The mixture was slurried for 30 minutes washed and dried. The product was analysed by XRF.

Zeolite 3 (According to the First Method)

The procedure of example B was repeated, except that prior to adding the zeolite slurry to the zinc sulphate solution, the pH of the zeolite slurry was reduced to pH 5 using 0.5 M sulphuric acid solution.

Zeolites 4, 5 and 6 (all according to the first method) are similar to example 1 except that the pH of the zeolite slurry was lowered to pH 6, 7 and 9 respectively.

From XRF analysis molar ratios of NasO (z from Formula III) and ZnO (w from Formula III) were obtained and these results as well as the combined ratios are given in Table 1 below:

TABLE 1

| Sample | $Na_2O/Al_2O_3$ (z) | $ZnO/Al_2O_3$ (w) | $Na_2O + ZnO/Al_2O_3$ (z + w) |
|---|---|---|---|
| Zeolite 1 | 0.58 | 0.65 | 1.21 |
| Zeolite 2 | 0.55 | 0.67 | 1.22 |
| Zeolite 3 | 0.43 | 0.52 | 0.95 |
| Zeolite 4 | 0.44 | 0.57 | 1.01 |
| Zeolite 5 | 0.47 | 0.58 | 1.05 |
| Zeolite 6 | 0.51 | 0.63 | 1.14 |

The above table clearly shows that whilst both the first two zeolite samples (1 and 2) result in products that are out by about 20% from the desired stoichiometry, the ion exchange process of the first method results compounds with (w+z) closer to the value required for stoichiometry. The table also shows that the combined ratio (w+z) increases with the increase pH of the zeolite slurry. The excess exchange observed in the comparative examples may be due to the high pH of the zeolite slurry resulting in the formation of some insoluble zinc species.

Scanning Electron Microscopy

Figure 4:
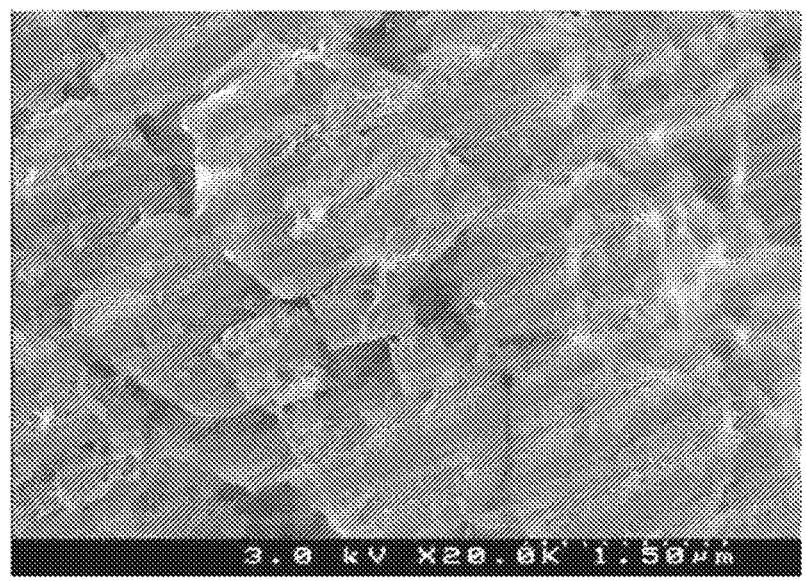
FIG. 4 is an electron scanning micrograph of Zeolite 2 of Example 3.
Figure 5:
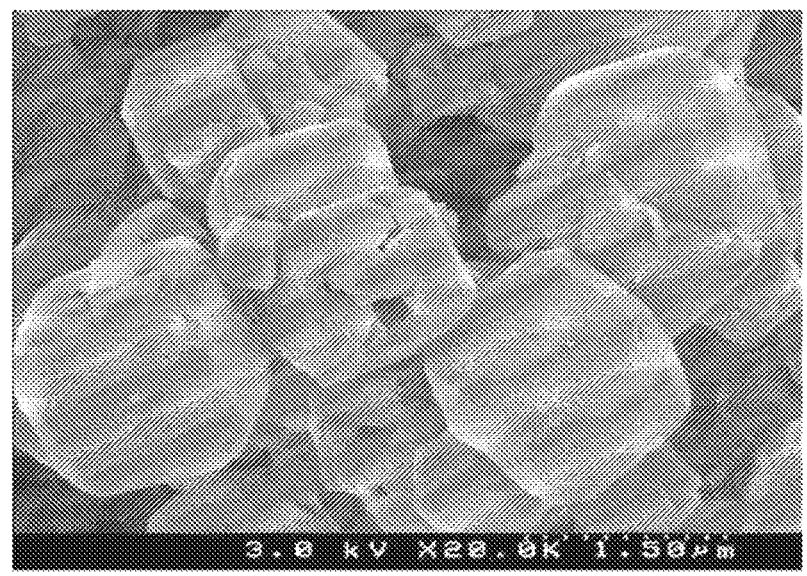
FIG. 5 is an electron scanning micrograph of Zeolite 4 of Example 3.

Scanning electron microscopy (SEM) was carried out on samples of Zeolite 2 and Zeolite 4 and the electron scanning micrographs are shown in FIGS. 4 and 5. In each of FIGS. 4 and 5, the broken lines represent a length of 1.5.

For FIG. 4, the prior art ion exchange process of Zeolite 2 results in second (exchanged) zeolite crystals with solid crystallites presumably of non-zeolitic species covering their surfaces. In FIG. 5, the second (exchanged) zeolite crystals resulting from the first method show clean surfaces which do not appear to be contaminated with non-zeolitic species.

Nitric Oxide Absorption Capacity Samples of zinc exchanged Zeolites 2 and 4 were first dehydrated at 300° C. in vacuo for 3 hours. The samples were then cooled to room temperature and exposed to approximately 2 atm. pressure of dry NO gas for 30 minutes. The excess NO was allowed to escape and the samples were flushed with dry nitrogen to ensure the removal of any physisorbed NO.

Nitric oxide assay was performed using a Sievers® NOA 280i chemiluminescence nitric oxide Analyser. To measure NO release from the samples, nitrogen gas of known humidity was passed over the samples and the resultant gas was directed into the analyser and the concentration of NO was recorded overtime and integrated to obtain the total nitric oxide absorption capacity. The absorption capacities for Zeolites 2 and 4 are given below in Table 2:

TABLE 2

| Sample | NO Absorption Capacity (mmol/g zeolite) |
|---|---|
| Zeolite 2 | 0.95 |
| Zeolite 4 | 1.25 |

The method described as the first method hereinbefore provides exchanged zeolites with significantly better NO adsorption capacity than conventional ion exchange methods.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" Is used the item can include a portion and/or the entire item unless specifically stated to the contrary.

We claim:

1. A nitric oxide-releasing dressing composition for use as a skin dressing comprising:
   i) between 30% and 60% by weight of an elastomeric-adhesive composition comprising an elastomeric polymer in combination with one or more water-soluble or water-swellable hydrocolloids;
   wherein the elastomeric polymer is selected from the group consisting of: natural or synthetic rubber or mixtures thereof, block copolymers of styrene/butadiene, polybutenes and polyacrylates; and
   the one or more water-soluble or water-swellable hydrocolloids are selected from the group consisting of: polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccharides, alginates, gelatine, xanthan gums, guar gums, and cellulosic polymers; and
   ii) between 40% and 70% by weight of a zeolite dispersed within the elastomeric-adhesive composition, said zeolite comprising releasably adsorbed nitric oxide.

2. A dressing composition according to claim 1 wherein the elastomeric adhesive composition comprises, based on the weight of the elastomeric-adhesive composition, from 15% to 70% by weight of the hydrocolloid and from 30% to 80% by weight of the elastomeric polymer.

3. A dressing composition as claimed in claim 1, wherein the elastomeric polymer is selected from polybutenes.

4. A dressing composition as claimed in claim 3, wherein the elastomeric polymer is polyisobutylene.

5. A dressing composition as claimed in claim 1, wherein the water-soluble or water-swellable hydrocolloids are selected from the group consisting of: polyvinyl alcohols, powdered pectin, gelatine, methyl cellulose, hydroxypropyl methyl cellulose, carboxymethylcellulose, hydroxypropyl cellulose and mixtures thereof.

6. A dressing composition as claimed in claim 1, wherein the water-soluble or water-swellable hydrocolloid is carboxymethylcellulose (CMC).

7. A dressing composition according to claim 1 wherein the zeolite is selected from the group consisting of; zeolite P, zeolite A, zeolite X, zeolite Y and mixtures thereof.

8. A dressing composition according to claim 7 wherein the zeolite is zeolite A.

9. A dressing composition according to claim 1 wherein the zeolite comprises a transition metal cation as an extra-framework metal cation, the metal selected from the group consisting of Co, Fe, Mn, Ni, Cu, Zn, Ag and a mixture thereof.

10. A dressing composition according to claim 9 wherein the extra-framework metal cation is selected from the group consisting of Zn, Cu, Ag and a mixture thereof.

11. A dressing composition according to claim 10 wherein the extra-framework metal cation is Zn.

12. A dressing composition according to claim 1 wherein the dressing composition releases nitric oxide at a generally uniform rate over an extended time period.

13. A dressing composition according to claim 1 wherein the zeolite is a dry zeolite.

14. A dressing composition according to claim 1 wherein the volume mean particle diameter of the zeolite is from 0.1 to 20 μm.

15. A dressing for application to skin comprising a backing layer holding a dressing layer comprising a skin contacting surface and a dressing composition according to claim 1.

16. The dressing of claim 15 further comprising a release liner removably attached to the skin-contacting surface of the dressing layer.

17. A method for the treatment of a human or animal body comprising applying to the human or animal body the dressing composition according to claim 1.

18. The method for treatment of claim 17 wherein the treatment is selected from the group consisting of: treatment of wounds, treatment of erectile dysfunction, treatment of anorgasmia, enhancement of transdermal drug delivery, vasodilation as a precursor to surgical insertion, treatment of skin diseases, treatment of neuropathy and treatment of inflammation.

19. A dressing composition according to claim 14 wherein the volume mean particle diameter of the zeolite is from 0.5 to 10 μm.

* * * * *